United States Patent [19]

Abe et al.

[11] E Re. 29,980

[45] Reissued May 1, 1979

[54] METHOD OF OBTAINING UROKINASE

[75] Inventors: Tsutomu Abe; Yasuo Hashino; Hidehiko Kobayashi, all of Fuji, Japan

[73] Assignee: Asahi Kasei Kogyo Kabushiki Kaisha, Osaka, Japan

[21] Appl. No.: 856,057

[22] Filed: Nov. 30, 1977

Related U.S. Patent Documents

Reissue of:

[64] Patent No.: 4,028,187
Issued: Jun. 7, 1977
Appl. No.: 701,930
Filed: Jul. 1, 1976

[30] Foreign Application Priority Data

Jul. 4, 1975 [JP] Japan ..... 50-81969

[51] Int. Cl.[2] ..... C07G 7/026
[52] U.S. Cl. ..... 195/66 B
[58] Field of Search ..... 195/66 B

[56] References Cited

U.S. PATENT DOCUMENTS

| | | | |
|---|---|---|---|
| 3,723,251 | 3/1973 | Ogawa et al. | 195/66 B |
| 3,957,582 | 5/1976 | Stried et al. | 195/66 B |

*Primary Examiner*—Lionel M. Shapiro
*Attorney, Agent, or Firm*—Sprung, Felfe, Horn, Lynch & Kramer

[57] ABSTRACT

A method of obtaining urokinase directly from human urine comprising contacting human urine with an acrylonitrile polymer of a unique porous structure formed at the time of polymerization for formation of the polymer and having a porosity of not less than 10% and a specific surface area of *not less than* 5 $m^2/g$. and subsequently eluting the urokinase adsorbed on the polymer. The acrylonitrile polymer employed in the method of the present invention has an excellent adsorption activity to urokinase and therefore, with use of an extremely small amount of the adsorbent, the satisfactory results can be obtained. Moreover, the porous polymer of the present method can also be utilized for purification of low purity crude urokinase obtained by the prior art methods.

13 Claims, No Drawings

METHOD OF OBTAINING UROKINASE

Matter enclosed in heavy brackets [ ] appears in the original patent but forms no part of this reissue specification; matter printed in italics indicates the additions made by reissue.

This invention relates to a method of obtaining urokinase.

More particularly, it is concerned with an improved and commercially advantageous method for obtaining urokinase from human urine which comprises intimately contacting human urine with a specific acrylonitrile polymer to adsorb urokinase contained in said urine on said polymer and eluting said adsorbed urokinase from said polymer.

Urokinase, as well-known in the art, is one of the enzymes which is present in a minor amount in human urine and effective in the treatment of various types of thrombosis. Additionally, the enzyme has recently been found to be favorably usuable together with some kind of antitumor agents.

In the prior art, there have been proposed for obtaining urokinase from human urine various methods wherein barium sulfate, a silica gel, an ion exchanger or an acrylonitrile type synthetic fiber is used as an adsorbent. Among the previous methods, a method wherein a protein having a peculiar adsorptive activity to urokinase, namely, an urokinase inhibitor is employed as an adsorbent (Japanese Patent Application Laid-open Specification No. 133589/1974) and another method wherein a conventional acrylonitrile type synthetic fiber is employed as an adsorbent (Japanese Patent Application Publication No. 10232/1973) are known for directly obtaining urokinase from human urine. In general, it is the most troublesome matter that a large quantity of fresh urine should be collected for obtaining urokinase in the art, since infinite labor would have to be expended for collecting and conveying numerous receiving vessels attached to urinals, which might be, in some cases, specially modified for such a purpose. Further, it has generally been recognized that discharged urine should be treated within about 8 hours after urination due to a drastic reduction in urokinase activity during prolonged storage of collected urine at room temperature. The aforesaid method using urokinase inhibitor presents the problem that the adsorbent is difficult to produce at a low cost and by mass production and thus the method may be inadequate for working on an industrial scale. Another known method using a polyacrylonitrile fiber is said to be satisfactory to some extent but has a problem in poor adsorption efficiency.

However, we have made extensive and intensive studies in order to meet the rapidly increasing demand for urokinase and develop a more convenient and inexpensive method for obtaining urokinase in human urine without any complicated working for collection of urine in the prior art. As a result of our studies, it has been unexpectedly found that a highly efficient obtainment of urokinase in a higher purity directly from human fresh urine can be accomplished by using as an adsorbent a porous acrylonitrile polymer of a porous structure formed at the time of production of the polymer and having a porosity of not less than 10% and a specific surface area of not less than 5 $m^2$g.

It is, accordingly, a primary object of this invention to provide an improved and advantageous method of directly obtaining urokinase from human urine without any pretreatment of urine.

The foregoing and other objects, features and advantages of the present invention will be apparent to those skilled in the art from the following detailed description and appended claims.

According to this invention, there is provided a more efficient method of obtaining urokinase from human urine comprising contacting human urine with a porous acrylonitrile polymer of a porous structure formed at the time of production of the polymer and having a porosity of not less than 10% and a specific surface area of *not less than* 5 $m^2$/g. to adsorb urokinase onto said acrylonitrile polymer and subsequently eluting the urokinase from said acrylonitrile polymer.

The term "acrylonitrile polymer" as used herein is contemplated to include polyacrylonitrile and a copolymer containing at least 30% by weight of acrylonitrile. In case of said copolymer, a comonomer polymerizable with acrylonitrile for the present copolymer may include, for example, an olefin such as isobutene, 1-hexene and the like; a vinyl ether such as ethyl vinyl ether, butyl vinyl ether and the like; a haloolefin such as vinylidene chloride, vinyl chloride, tetrafluoroethylene and the like; a diene such as butadiene, isoprene and the like; an acrylate or methacrylate such as acrylic or methacrylic acid, methyl acrylate or methacrylate, butyl acrylate or methacrylate, 2-hydroxyethyl acrylate or methacrylate, N,N-diethylaminoethyl acrylate or methacrylate and the like; a vinyl ester such as vinyl benzoate, vinyl acetate and the like; an aromatic vinyl monomer such as styrene, α-methylstyrene and the like; an amide type vinyl monomer such as acrylamide, methacrylamide, vinyl pyrrolidone and the like; a nitrile such as methacrylonitrile, vinylidene cyanide and the like; maleic anhydride; a maleimide derivative; styrenesulfonic acid, methallylsulfonic acid and a salt thereof; a basic vinyl monomer such as vinyl pyridine, vinylimidazole and the like, the above-named comonomers being optionally used alone or in combination.

The acrylonitrile polymer adsorbent, namely porous acrylonitrile polymer, to be employed in the method of the present invention is, as mentioned hereinabove, characterized by its specific porous structure formed at the time of polymerization for producing said polymer and having a porosity of not less than 10% and a specific surface area of not less than 5 $m^2$/g. It is to be noted that such specific porous structure formed at the time of formation of the acrylonitrile polymer and having a porosity of not less than 10%, and a specific surface area of not less than 5 $m^2$g., is critical for the prominent effect of the present invention. There are not upper limits in respect of porosity and specific surface area but there may practically be employed a porous acrylonitrile polymer having a porosity of 10 to 50% and a specific surface area of 5 to 100 $m^2$g. in view of ready production of a porous material.

The acrylonitrile polymer to be employed in the method of the present invention may be prepared by solution polymerization, suspension polymerization or emulsion polymerization using acrylonitrile alone or in combination with at most 70% by weight of one or more of the above-mentioned comonomers. The solution polymerization, suspension polymerization or emulsion polymerization may be conducted in a liquid medium in which the acrylonitrile polymer to be formed is substantially insoluble, for example water, an alcohol, a hydrocarbon, an ester, a nitrile and the like, using a radical polymerization initiator of, for example azo type, peroxide type, redox type or the like. The monomer may be soluble or dispersible in the liquid medium. When water is employed as a dispersion medium, an emulsifying agent may be used in an amount ordinarily employed for emulsion polymerization. Of the above-mentioned liquid media, an aqueous medium containing 50 to 100% by volume of water is preferably employed. In polymerization, the amount ratio of a monomer to a liquid medium may be in the range of 1:2 to 1:10. In this connection, it is noted that when the conversion rate of monomer to polymer is suppressed at a level of not more than about 30%, the monomer itself may serve as a liquid medium. The polymerization temperature may be varied essentially depending on the kind of initiator employed, but may generally be in the range of 40° to 150° C., preferably 40° to 80° C.

According to the above-mentioned polymerization method, there may be prepared a porous acrylonitrile polymer employable in the method of the present invention. Illustratively stated, by the polymerization method as mentioned above, the obtained acrylonitrile polymer is caused to have a specific porous structure at the time of polymerization so that the porous polymer has a specific shape of pore and a physicochemically active surface suitable for adsorbing urokinase. When an aqueous medium containing at least 50% by volume of water is employed, especially good results can be obtained.

After completion of the polymerization, the porous acrylonitrile polymer is obtained in the form of a slurry. The slurry may be used as such, after washing. Alternatively, the polymer may be used in the form of powder having a particle size of 10 to 500μ. For this purpose, the slurry may be washed, subjected to filtration and dried to form a powder. Further, any other desired form or shape of the porous acrylonitrile polymer may be favorably employed in the method of the present invention, so long as the unique porous structure formed at the time of polymerization is maintained. For example, the porous acrylonitrile polymer may advantageously be employed in the form as coated on a support or in the form as coagulated. In the former case, the polymer can be made easy for handling since the shape of a support is variable. In the latter case, the slurry or powder having a small particle size obtained by the polymerization can be formed into one having a relatively coarse particle size of 50 to 1,000μ by various coagulation methods.

As the support employable, there can be mentioned those of any desired shape as far as it does not hinder obtaining urokinase, for example granules such as glass beads and polystyrene beads having a diameter of 50 to 1,000μ; and 1 to 50 denier—filaments or staple fibers of various kinds of materials (e.g. cellulose or glass fiber) or clothes or nets made therefrom. As a method of coating the support with a porous acrylonitrile polymer, there may be employed (A) a method of polymerizing an acrylonitrile monomer or a mixture thereof with a comonomer in the presence of such support and (B) a method of applying the porous polymer onto the support through an appropriate adhesive medium to form a coating of about 10 to 500μ in thickness. In the method (A), the polymerization is conducted in a liquid medium in which both the support and the porous acrylonitrile polymer to be formed are substantially insoluble. The amount ratio of the support to the acrylonitrile polymer is varied depending on the kind of support and the conversion of the monomer to polymer but may be generally in the range of 4:1 to 1:5. As illustrative examples of the method (B), there may be employed: (B-1) An adhesive material (which may have a softening point higher or lower than that of polyacrylonitrile but may preferably have a lower softening point than that of polyacrylonitrile for ease of operation), for example polyvinyl acetate, block SBR or the like, is applied onto the support and the porous acrylonitrile polymer powder is applied thereon at a temperature higher than the softening point of the adhesive material to coat the support in a thickness of 10 to 500μ, followed by cooling; (B2) An appropriate polymer such as polyvinyl acetate, polystyrene, block SBR, polymethyl methacrylate or the like is dissolved in a solvent (in which the porous acrylonitrile polymer is substantially insoluble) such as aliphatic hydrocarbons, aromatic hydrocarbons, esters, ketones and the like, the resultant solution is thinly applied onto the support, and the porous acrylonitrile polymer powder is applied thereon before drying of the polymer solution, followed by drying; and (B-3) An appropriate thermoplastic resin such as polystyrene, polyethylene, polymethyl methacrylate or the like is heated to cause the surface thereof to be soften and the porous acrylonitrile polymer powder is applied onto the surface, followed by cooling. As a method of making the slurry or powder of porous acrylonitrile polymer into a coagulated form, there may be employed, for example a method of making the porous acrylonitrile polymer wet with water when a slurry is employed, it may be used as such and when a powder is employed, it is made wet with addition of water) to have a water content of about 50 to 500% by weight and then applying a pressure of 1 to 20 kg./cm$^2$ thereto to effect molding or a method of admixing the porous acrylonitrile polymer with a small amount of an adhesive material to make a coagulated form having at most 30% of the overall surface masked through the adhesive material.

In practicing the method of the present invention, 1 liter of human urine is contacted directly with 0.1 to 0.3 g. of a porous acrylonitrile polymer used as an adsorbent to adsorb urokinase in the urine onto the adsorbent. Although more than 0.3 g. of adsorbent may be employed, there is not any increase in obtainment of urokinase and specific activity of the obtained urokinase. With use of an extremely small amount of the adsorbent, a sufficient effect is obtained in the method of this invention and, therefore, the method of this invention is economically advantageous. Moreover, the spent adsorbent can be thrown away without any fear of pollution. The adsorption may be conducted at a temperature of not more than 50° C. but is usually conducted at a temperature of 0° C. to room temperature so that a fear of deactivation of the urokinase may be avoided. After the urokinase is adsorbed on the adsorbent, the remaining urine is removed by washing and then the absorbed urokinase is eluted with an aqueous alkali solution. As the alkali solution, there may be employed, for example an aqueous amine or a 1 to 20% by weight aqueous ammonia solution or a 0.01 to 0.05% by weight aqueous solution of sodium hydroxide. Of them, an aqueous ammonia solution may be most preferably employed. The elution is accomplished instantaneously. The temperature condition for the elution is the same as in the adsorption procedure. The aqueous alkali solution may be employed in an amount of 5 to 100 ml. per 1 g. of the adsorbent containing urokinase.

Both the adsorption and elution operations may be conducted using a batch system or column system.

As depicted above, the acrylonitrile polymer in this invention has advantages over those adsorbents proposed in the prior arts and, especially, unique merit as compared with the acrylonitrile fiber disclosed in the aforementioned Japanese Patent Publication No. 10232/1963. These unexpectedly excellent characteristics of the present adsorbent will be briefly summarized, for the purpose of illustration only, as seen below.

1. The pH value of human urine in healthy subjects is known to be variable over a broad range from 4.5 through 8.0 depending upon diets, labor conditions and other factors, but the present adsorbent has an excellent adsorption activity (in adsorption amount and rate of adsorption) over the broadly varied pH range and, in particular, affords a saturated adsorption amount 5 to 10 times that of the prior acrylonitrile fiber type adsorbent.

2. Various contaminants are known to be present in large quantities in urine along with urokinase, but the present adsorbent shows a particularly high selectivity in adsorption of urokinase, which results in simplification of urokinase purification.

3. It has been found that stability of the adsorbed urokinase on the present adsorbent is much higher than expected. More specifically, where the present adsorbent is placed within a urinal or into a waste pipe attached to a urinal at the lower part thereof in the form of a packed tube, it is easy and satisfactory to collect the adsorbent therefrom without any necessity of laborious working for collecting urine as in the prior art. Furthermore, the adsorbed urokinase on adsorbents is not eluted with the flush water in the urinal. In addition, it has been surprisingly found that the adsorbed urokinase on the present adsorbent hardly undergoes any deactivation during the lapse of time even at room temperature.

As stated before, since the adsorbent employed in the method of the present invention has an excellent adsorption activity for urokinase, the method is applicable to not only obtaining urokinase directly from human urine but also purification of crude urokinase obtained by other methods, for example the prior art method.

The definition and measurement of "porosity" used in this invention are in accordance with those described in H. G. Cassidy and K. A. Kun: "Oxidation—Reduction Polymers" Published by Interscience Publishers, P. 155–167. The measurement of specific surface area was done by BET surface measuring apparatus using nitrogen.

EXAMPLE 1

A monomer mixture of 92% by weight of acrylonitrile and 8% by weight of methyl acrylate was dispersed in water and the aqueous suspension was subjected to suspension polymerization with potassium persulfate-ferrous chloride redox type initiator to afford a porous powder (Adsorbent I), which has a porosity of 25% and a specific surface area of 50 $m^2/g$.

The Adsorbent I, and, as a control, "Vonnel" fibers of about 3 denier (trade name of acrylic fiber manufactured by the Mitsubishi Rayon K.K., Japan), precipitated barium sulfate (manufactured by Sakai Kagaku K.K., Japan) and active carbon powder (Norit A, trade name of active charcoal available from American Norit Co., Ltd., U.S.A.) were employed for test in each 0.07 g. portion.

Each adsorbent was added to 1 liter of fresh urine (pH 6.3) and stirring was continued for 2 hours at about 4° C. to prevent deactivation.

After completion of the adsorption, the adsorbent was filtered off. The filtrate thus obtained and another portion of untreated fresh urine were dialyzed for 24 hours at 4° C. against 0.1 M. sodium phosphate buffer (pH 6.5) and then respective urokinase activity was assayed by the fibrin plate method. The saturated adsorption amount of each adsorbent was calculated based on the difference between the urokinase activity of dialyzed untreated fresh urine and that of the dialyzed filtrate.

The results are summarized in Table I.

Table 1

Adsorption efficiency of test adsorbents

| Test Adsorbent | Saturated Adsorption Amount (international unit/g. of adsorbent) |
|---|---|
| Adsorbent I | 52,000 |
| Vonnel Fiber | 6,800 |
| Precipitated $BaSO_4$ | 1,500 |
| Active Carbon | 12,000 |

It will be apparent from the above results that the Adsorbent I of this invention has a highly superior adsorption activity to the other control adsorbents and thus makes it feasible to obtain a much larger amount of urokinase with a smaller amount of the adsorbent.

EXAMPLE 2

Porous polymers as indicated below were prepared with varied monomer compositions in the same manner as in Example 1 and tested for their adsorption efficiency according to the same procedures as in Example 1.

The results are summarized in Table 2.

Table 2

Adsorbent Compositions and saturated adsorption amounts

| Test Adsorbent | | | | Saturated Adsorption Amount |
|---|---|---|---|---|
| | | Polymer | | |
| No. | Monomers (% by weight) | Porosity (%) | Specific Surface Area ($m^2/g$) | (international unit/g. of adsorbent) |
| 1 | Acrylonitrile (100) | 20 | 29 | 47,000 |
| 2 | Acrylonitrile (85) Methyl acrylate (15) | 27 | 70 | 51,000 |
| 3 | Acrylonitrile (75) Acrylamide (25) | 14 | 15 | 43,000 |
| 4 | Acrylonitrile (40) Vinyl chloride (60) | 21 | 35 | 32,000 |
| 5 | Acrylonitrile (80) Acrylic acid (20) | 16 | 20 | 46,000 |
| 6 | Control Vinyl chloride (100) | 15 | 30 | 9,800 |
| 7 | Control Styrene (100) | 8 | 25 | 8,300 |

EXAMPLE 3

0.2 g of each of adsorbent I of the above Example 1, "Exlan" fibers of about 3 denier (trade name of acrylic fiber manufactured by Nihon Exlan Kogyo K.K., Japan) and Amberlite IRC-50 (ion exchange resin manufactured by Rohm and Haas Co., Ltd., U.S.A.) were employed for testing. Each adsorbent was added to 1 liter of fresh urine (pH 6.1) and stirring was conducted for 30 minutes as 4° C. Then, the adsorbent was filtered off through a glass fiber. The filtrate was dialyzed in the same manner as in Example 1 and assayed to determine residual urokinase activity. Adsorption (%) was calculated upon the measured activity value.

On the other hand, the separated adsorbent on a glass filter was washed with 50 ml. of a 1 N aqueous solution of sodium chloride and 30 ml. of distilled water and the adsorbed urokinase was eluted from the adsorbent with 20 ml. of 4% aqueous ammonia. The 4% aqueous ammonia eluate containing urokinase was dialyzed in the same manner as in Example 1 and assayed for urokinase activity, together with the determination of proteins according to the Lowry method [J. Biol. Chem., 193, 265 (1951)]. Urokinase recovery compared to the urokinase initially contained in the fresh urine as well as specific activity of the urokinase were determined upon the measured values.

The results are summarized in Table 3.

Table 3

Effects of adsorbents on recovery and specific activity of urokinase

| Test Adsorbent | Adsorption % | Recovery % | Specific Activity (international unit/mg. of protein) |
|---|---|---|---|
| Adsorbent 1 | 100 | 91 | 4,900 |
| Exlan Fiber | 45 | 30 | 3,100 |
| Amberlite IRC-50 | 42 | 38 | 900 |

It will be apparent from the above results that the adsorbent in this invention can effect not only recovery of a much larger amount of urokinase using a smaller amount of adsorbent but also a higher specific activity of the obtained crude urokinase as compared with other prior art methods, which leads to a considerable simplification of the urokinase purification process.

EXAMPLE 4

10 g of each of porous polyacrylonitrile designated as No. 1 in the above Example 2 and "Vonnel" fiber as a control were employed as test adsorbents. Each adsorbent was charged into a column with an inner diameter of 3 cm. and then five 2 liter-portions (total 10 liters) of fresh urine (pH 6.3–6.7) were passed through the column every 4 hours. Every urine effluent was dialyzed and assayed for urokinase activity in the same manner as in Example 1. After about 20 hours from the first pass of the urine, the column was washed with a successive flow of 500 ml. of a 1 N aqueous solution of sodium chloride and 300 ml. of distilled water and then the adsorbed urokinase was eluted with 200 ml. of 4% aqueous ammonia. The eluate containing urokinase was determined for urokinase activity and proteins in the same manner as in the above Example 3. Recovery and specific activity of urokinase are shown in Table 4.

Table 4

| Test Adsorbent | Recovery % | Specific Activity (international unit/mg. of protein) |
|---|---|---|
| Porous Acrylonitrile Polymer | 76 | 4,600 |
| Vonnel Fiber | 27 | 1,800 |

Average residual urokinase activity in the urine effluent was 0% for the polyacrylonitrile and 14% for Vonnel fiber.

From the foregoing, it is fairly concluded that the adsorbed urokinase on the porous polymer is far more stable at room temperature as compared with the Vonnel fiber.

EXAMPLE 5

28 g. of acrylonitrile and 22 g. of styrene were mixed with 30 ml. of toluene and 0.5 g. of azobisisobutyronitrile was added to the mixture and prefectly dissolved. The obtained solution was dispersed in 500 ml. of water and the aqueous suspension was subjected to suspension polymerization at 60° C. and under stirring. After completion of the polymerization the obtained polymer (diameter of particle: 150–300μ) was filtered, washed sufficiently with water and then with methanol, and stored in water. The obtained powder of this polymer has a porosity of 12% and a specific surface are of 6 $m^2/g$. 0.3 of the powder was added to 1 liter of urokinase sample prepared by adjusting the pH to 8.5 and removing the precipitates by filtration, and stirring was conducted for about 1.5 hour to effect adsorption. In the same manner as in Example 3 urokinase activity and protein content were measured after washing, desorption and dialysis. Recovery of urokinase was 88% and urokinase activity was 6,100 I.U. (international unit)/mg. of protein as compared with 18% and 2,200 I.U/mg. of protein in case of 0.3 g. of Vonnel fiber used as adsorbent.

EXAMPLE 6

35 g. of acrylonitrile, 10 g. of methyl acrylate and 5 g. of 2-vinylpyridine were dispersed in 500 ml. of water premixed with 30 g. of cellulose pulp, and the aqueous suspension was subjected to suspension polymerization with a potassium persulfate-ferrous chloride redox type initiator. 70 g. of cellulose pulp coated with polyacrylonitrile type porous powder were obtained and had a porosity of 36% and a specific surface area of 80 $m^2/g$.

By using 0.2 g. of this porous powder, 1 liter of urine was treated in the same manner as in Example 3 to obtain urokinase. Recovery and specific activity of urokinase were 88% and 5,300 I.U./mg. of protein, respectively.

EXAMPLE 7

Polyacrylonitrile type porous powder obtained in Example 1 was wetted with water and pressed at 5 $kg./cm^2$. to form a slab. The slab was dried, pulverized and sieved to collect in a particle size of 20 to 40 mesh. By using 0.2 g. of this adsorbent 1 liter of urine was treated in the same manner as in Example 3 to obtain urokinase. Recovery and specific activity of urokinase were 85% and 5,100 I.U./mg. of protein, respectively.

EXAMPLE 8

Acrylonitrile was emulisifed in water mixed with sodium alkylsulfonate and polymerized with potassium persulfate-sodium hydrogen sulfite redox type initiator. There was obtained a porous powder having an average particle diameter of 10μ., a porosity of 15% and a specific surface diameter of 35 $m^2/g$. By using 0.3 g. of the porous powder 1 liter of urine was treated in the same manner as in Example 3 to obtain urokinase. Recovery and specific activity of urokinase were 95% and 4,800 I.U./mg. of protein, respectively.

EXAMPLE 9

A monomer mixture of 92% by weight of acrylonitrile and 8% by weight of methyl acrylate was radical-polymerized in solvents as shown in Table 5 at 60° C. and porous polymers were obtained. Saturated adsorption amounts of urokinase in adsorbents were measured in the same manner as in Example 1. Porosity and specific surface area are also shown in the following table.

Table 5

Effects of solvents on porosity and specific surface area of the resultant adsorbent

| No. | Solvent | Polymerization Initiator | Porosity % | Specific Surface Area ($m^2/g$.) | Saturated Adsoption Amount (I.U./g. of adsorbent |
|---|---|---|---|---|---|
| 1 | Methanol | Azobisisobutyronitrile | 18 | 20 | 35,000 |
| 2 | n-Hexane | lauroyl peroxide | 15 | 10 | 32,000 |
| 3 | Methanol-water (40 : 60 volume ratio) | Potassium persulfate-ferrous chloride | 24 | 35 | 49,000 |

COMPARATIVE EXAMPLE 1

A polymer obtained in Example 1 was dissolved in a 68% by weight of aqueous solution of nitric acid to obtain a concentration of 10% (w/v). The solution was poured into a large amount of water under vigorous stirring and the resulting polymer was collected by filtration, washed and dried. The obtained powder had a porosity of 11% and a specific surface area of 25 $m^2/g$. A saturated adsorption amount of urokinase in the adsorbent was 7,300 I.U./g. of adsorbent.

COMPARATIVE EXAMPLE 2

1 part by weight of a monomer mixture containing 60% by weight of acrylonitrile and 40% by weight of vinyl acetate was dispersed in 1.5 part by weight of water and the aqueous dispersion was subjected to polymerization with a potassium persulfate—ferrous chloride redox type initiator at 55° C. and under high speed stirring. The obtained polymer had a porosity of 5% and a specific surface area of 1 $m^2/g$. A saturated adsorption amount of urokinase in the adsorbent was measured according to the same procedures as in Example 1, and showed 8,200 I.U./g. of adsorbent.

COMPARATIVE EXAMPLE 3

1 part of weight of monomer mixture containing 50% by weight of acrylonitrile, 30% by weight of styrene and 20% by weight of methyl methacrylate in which azobisisobutyronitrile was dissolved at room temperature, was dispersed in 1.2 part by weight of aqueous solution of sodium dodecylbenzenesulfonate with a concentration of 0.05% (w/v), and the aqueous dispersion was subjected to polymerization at 65° C. The obtained polymer had no porosity and a specific surface area of 0.1 $m^2/g$. The polymer was dissolved in 68% by weight of aqueous solution of nitric acid in the same manner as in Comparative Example 1 and the polymer solution was poured into a large amount of water under high speed stirring. The obtained powder had a porosity of 10% and a specific area of 23 $m^2/g$. A saturated adsorption of urokinase in the adsorbent was measured according to the same procedures as in Example 1, and showed 7,500 I.U./g. of adsorbent.

What is claimed is:

1. A method of obtaining urokinase from human urine comprising contacting human urine with an acrylonitrile polymer of a porous structure having a porosity of not less than 10% and a specific surface area of *not less than* 5 $m^2/g$. to adsorb urokinase onto said acrylonitrile polymer, said porous structure having been formed at the time of polymerization for formation of the polymer, and subsequently eluting the urokinase from said acrylonitrile polymer having the urokinase adsorbed thereon.

2. A method according to claim 1 wherein said acrylonitrile polymer is a homopolymer or a copolymer of acrylonitrile.

3. A method according to claim 2 wherein said polymer is a copolymer and contains at least 30% by weight of acrylonitrile based on the copolymer of acrylonitrile.

4. A method according to claim 1 wherein said porosity is 10 to 50%.

5. A method according to claim 1 wherein said specific surface area is 5 to 100 $m^2/g$.

6. A method according to claim 1 wherein said acrylonitrile polymer is one obtained by solution polymerization, suspension polymerization or emulsion polymerization of a corresponding monomer in a liquid medium selected from the group consisting of water, an alcohol, a hydrocarbon, an ester, a nitrile and mixtures thereof, said monomer and said liquid medium being employed in an amount ratio of 1:2 to 1:10.

7. A method according to claim 6 wherein said liquid medium is an aqueous system containing at least 50% by volume of water.

8. A method according to claim 1 wherein said acrylonitrile polymer is in the form of an aqueous slurry or a powder.

9. A method according to claim 1 wherein said acrylonitrile polymer is in the form of a coating on a support.

10. A method according to claim 1 wherein said acrylonitrile polymer is in the form as coagulated.

11. A method according to claim 1 wherein said acrylonitrile polymer is employed in an amount of 0.1 to 0.3 g. per liter of the human urine.

12. A method according to claim 1 wherein the eluting is effected using an aqueous alkali solution.

13. A method according to claim 12 wherein said aqueous alkali solution is an aqueous solution of a member selected from the group consisting of ammonia, an amine and sodium hydroxide.

* * * * *